US011096755B2

(12) United States Patent
Frye et al.

(10) Patent No.: US 11,096,755 B2
(45) Date of Patent: Aug. 24, 2021

(54) SURGICAL TOOL MANAGEMENT SYSTEM

(71) Applicant: Frye Medical, LLC., Vacaville, CA (US)

(72) Inventors: Jeffrey Samuel Frye, Vacaville, CA (US); Milind Raghunath Dhond, Davis, CA (US)

(73) Assignee: FRYE MEDICAL, LLC., Vacaville, CA (US)

( * ) Notice: Subject to any disclaimer, the term of this patent is extended or adjusted under 35 U.S.C. 154(b) by 134 days.

(21) Appl. No.: 15/960,691

(22) Filed: Apr. 24, 2018

(65) Prior Publication Data

US 2019/0321121 A1    Oct. 24, 2019

(51) Int. Cl.
*A61B 46/23* (2016.01)
*A61B 50/15* (2016.01)
(Continued)

(52) U.S. Cl.
CPC .............. *A61B 46/23* (2016.02); *A61B 50/15* (2016.02); *A61B 50/20* (2016.02); *F16B 2/005* (2013.01); *F16B 2/10* (2013.01); *A44B 1/00* (2013.01); *A44B 17/00* (2013.01); *A61B 90/92* (2016.02); *A61B 2050/155* (2016.02); *F16B 1/00* (2013.01); *F16B 1/0071* (2013.01); *F16B 11/006* (2013.01); *F16B 2001/0028* (2013.01); *F16B 2001/0035* (2013.01)

(58) Field of Classification Search
CPC ......... A61B 46/23; A61B 46/00; A61B 46/10; A61B 50/20; A61B 50/15; A61B 50/22; A61B 50/24; A61B 50/10; A61B 2050/155; A61B 2050/21; A61B 2050/002; A61B 2050/0067; A61B 2050/007; A61B 2050/0074; A61B 2050/0082; A61B 2050/0083; A61B 2050/0085; A61B 90/92; A61B 2046/234; A61B 2046/236; A61B 90/57; A61G 7/0503; A61G 13/101; A61M 25/02; F16B 2/10; F16B 2/005; F16B 1/0071; F16B 2001/0028; F16B 2001/0035; F16B 11/006; F16B 1/00; A44B 1/00; A44B 17/00

See application file for complete search history.

(56) References Cited

U.S. PATENT DOCUMENTS 6,458,104 B2 * 10/2002 Gautsche ............ A61M 5/1418
                                              128/DIG. 26
8,505,748 B2 *  8/2013 Jones ................ A61B 17/06061
                                              206/370

(Continued)

*Primary Examiner* — Tarla R Patel
(74) *Attorney, Agent, or Firm* — Kali Law Group, P.C.

(57) ABSTRACT

Surgical tool management systems are presented including: a number of surgical tool holders for removably securing a number of surgical tools, where each of the surgical tool holders includes: a base, where the base includes a top surface and a bottom surface, an attachment element coupled with and along the bottom surface, where the attachment element removably couples with a surgical surface, and at least two opposing securing elements disposed along the top surface. In some embodiments, the surgical surface is selected from the group consisting of: a surgical curtain, a Mayo stand, and an instrument table. In some embodiments, the opposing securing elements include: a multi-purpose clip, a wire holder, and a tube clamp.

14 Claims, 5 Drawing Sheets

(51) Int. Cl.
*A61B 50/20* (2016.01)
*F16B 2/10* (2006.01)
*F16B 2/00* (2006.01)
*A61B 90/92* (2016.01)
*F16B 1/00* (2006.01)
*A44B 1/00* (2006.01)
*A44B 17/00* (2006.01)
*F16B 11/00* (2006.01)

(56) References Cited

U.S. PATENT DOCUMENTS

| | | | | |
|---|---|---|---|---|
| 9,127,786 B1 * | 9/2015 | Arratia | ............ | A61M 25/09 |
| 2003/0121811 A1 * | 7/2003 | Roshdy | ............ | B65D 77/26 |
| | | | | 206/363 |
| 2004/0073233 A1 * | 4/2004 | Jannot | ............ | A61B 17/06061 |
| | | | | 606/148 |
| 2004/0133078 A1 * | 7/2004 | Edoga | ............ | A61B 17/02 |
| | | | | 600/227 |
| 2007/0235038 A1 * | 10/2007 | Alinsod | ............ | A61B 17/02 |
| | | | | 128/849 |
| 2008/0076989 A1 * | 3/2008 | Hete | ............ | A61B 5/14552 |
| | | | | 600/323 |
| 2011/0083983 A1 * | 4/2011 | Walters | ............ | A61B 46/23 |
| | | | | 206/370 |

\* cited by examiner

_US 11,096,755 B2_

SURGICAL TOOL MANAGEMENT SYSTEM

FIELD OF INVENTION

The present invention relates to systems for managing surgical instruments and methods of use thereof.

BACKGROUND

During a medical procedure, many medical instruments, wires, catheters, and other medical devices are used. These devices may be difficult to keep organized, and may get contaminated, or even fall off the table. This requires the item to be discarded or re-sterilized, which costs extra money to replace or makes the medical procedure take even more time. Put simply, trying to secure an item to a sterile drape with a hemostat can be unwieldy and difficult. In addition, when utilizing a wet operating room towel or gauze on a medical device or wire, the towel or gauze can obscure the device or wire from sight making the device or wire difficult to locate. In some cases, the towel or gauze may cause the device or wire to fall off when the patient moves. Current methods of managing medical devices are time consuming and unreliable. There is a need in the industry for an efficient and reliable system to manage medical devices during a surgical procedure.

As such surgical tool management systems are provided herein.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented below.

Surgical tool management systems are presented including: a number of surgical tool holders for removably securing a number of surgical tools, where each of the surgical tool holders includes: a base, where the base includes a top surface and a bottom surface, an attachment element coupled with and along the bottom surface, where the attachment element removably couples with a surgical surface, and at least two opposing securing elements disposed along the top surface. In some embodiments, the surgical surface is selected from the group consisting of: a surgical curtain, a Mayo stand, and an instrument table. In some embodiments, the opposing securing elements include: a multi-purpose clip, a wire holder, and a tube clamp. In some embodiments, the multi-purpose clip includes: a clamping arm having an arm contact face; a clamping spring; and a pivot pin, and where the base further includes a base contact face. In some embodiments, the arm contact face and the base contact face is selected from the group consisting of: a flat face, a contoured face, a ribbed face, a curved groove face, a squared groove face, and a channeled face. In some embodiments, the attachment element is selected from the group consisting of: a snap, a clasp, a clamp, a hook and loop strip, an adhesive tape strip, a fabric pinch, a magnetic strip, and a button.

In other embodiments, surgical tool holders that removably secure a surgical tool are presented, the surgical tool holders including: a base where the base includes a top surface and a bottom surface, an attachment element coupled with and along the bottom surface, where the attachment element removably couples with a surgical curtain, and at least two opposing securing elements disposed along the top surface. In some embodiments, the opposing securing elements are selected from the group consisting of: a multi-purpose clip, a wire holder, and a tube clamp.

In other embodiments, methods for using a surgical tool management system are presented including: providing a surgical curtain; providing a number of surgical tool holders for removably securing a number of surgical tools, where each of the number of surgical tool holders includes: a base, where the base includes a top surface and a bottom surface, an attachment element coupled with and along the bottom surface, where the attachment element removably couples with a surgical curtain, and at least two opposing securing elements disposed along the top surface, where the opposing securing elements are selected from the group consisting of: a multi-purpose clip, a wire holder, and a tube clamp; securing the number of surgical tool holders with the surgical curtain; securing the number of surgical tools with the number of surgical tool holders; and during a procedure, removing any of the number of surgical tools from any of the number of surgical tool holders for immediate use.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

The present invention will now be described in detail with reference to a few embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

In still other instances, specific numeric references such as "first material," may be made. However, the specific numeric reference should not be interpreted as a literal sequential order but rather interpreted that the "first material" is different than a "second material." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

Figure 1:
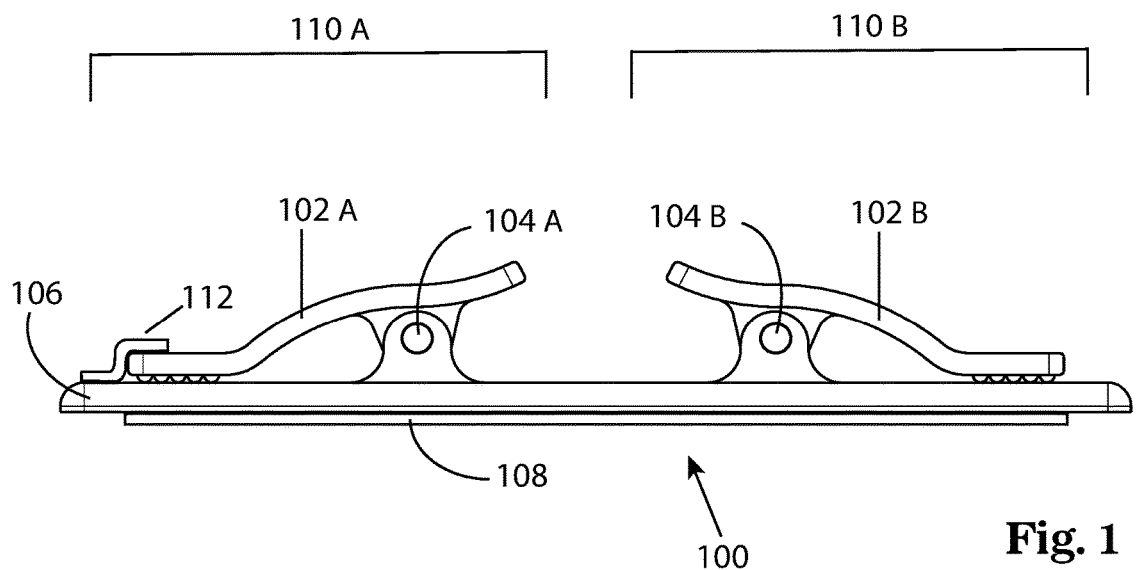
FIG. 1 is an illustrative representation of a surgical tool holder in accordance with embodiments of the present invention.

FIG. 1 is an illustrative representation of a surgical tool holder 100 in accordance with embodiments of the present invention. In particular, FIG. 1 illustrates surgical tool holder 100 in side view. In embodiments presented various types of opposing securing elements may be utilized alone or in combination. The opposing securing elements presented in this illustration are multi-purpose clips 110A and 110B. Multi-purpose clips may be utilized for securing any number of surgical tools. In addition, by simply changing the arm contact face of a multi-purpose clip embodiment, a customized gripping surface may be achieved. In embodiments, an arm contact face may be manufactured from a variety of materials including: a foam material, a polymeric material, a hydrophilic material, a rubber material, and a composite material without limitation. Arm contact faces will be discussed in further detail below for FIGS. 3B-3D. As illustrated, multi-purpose clips 110A and 110B include clamping arms 102A and 102B, which arms may be pivotally coupled with base 106 via pin 104A and 104B. In addition, as illustrated, an attachment element or layer 108 may be coupled with base 106 along the base's bottom surface. This attachment element may be utilized to couple the surgical tool holder with a surgical surface. As noted above, at times, a surgeon or surgical team may utilize a portion of a surgical surface such as a surgical curtain to lay out or organize surgical tools. In order to maintain order and secure surgical tools, an attachment element may be utilized to couple the surgical tool holder with the surgical surface. Surgical surfaces may include a surgical curtain, a Mayo stand, and an instrument table without limitation. In addition, attachment element embodiments may include: a snap, a clasp, a clamp, a hook and loop strip, an adhesive tape strip, a fabric pinch, a magnetic strip, and a button without limitation.

In some embodiments, each of the opposing securing elements may be manufactured from a phosphorescent material to aid in locating the surgical tool holder in an otherwise shaded or unlighted area. In addition, in some embodiments, the opposing securing elements may be color coded by surgical function or surgical type. In this manner, appropriate surgical tool holders may be easily selected by surgical team members. Further illustrated is breakable strip 112. In some examples, it may be desirable to include a breakable strip along the openings of the opposing securing elements such that the breakable strip is parted upon using the opposing securing elements. It may be appreciated that this feature may be utilized to indicate to a surgical team member that the surgical tool holder has been used to secure a surgical tool. If no tool is present in the surgical tool holder and the breakable strip is parted, then this may be an indication that a surgical tool is missing. By identifying the use of the holder, lost tools may be avoided in some examples.

Figure 2:
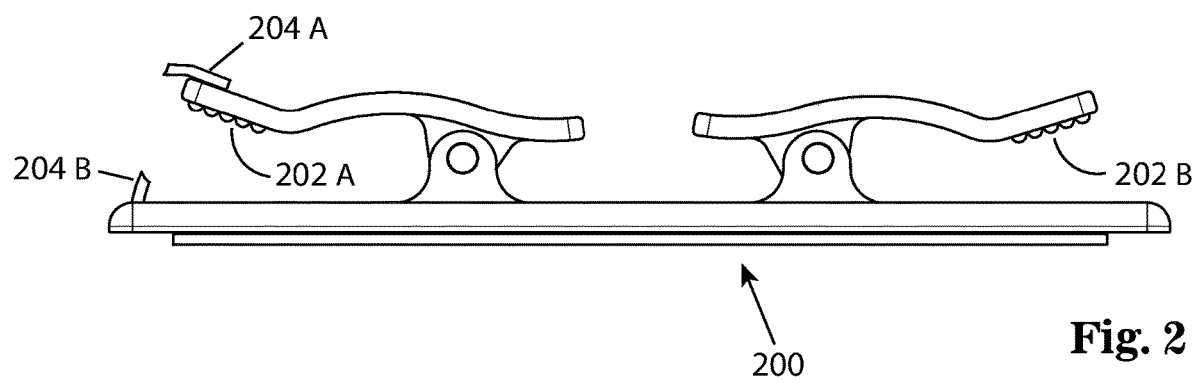
FIG. 2 is an illustrative representation of a surgical tool holder in accordance with embodiments of the present invention.

FIG. 2 is an illustrative representation of a surgical tool holder 200 in accordance with embodiments of the present invention. In particular, FIG. 2 illustrates surgical tool holder 200 in side view. As above, opposing securing elements presented in this illustration are multi-purpose clips. In this illustration, however, the multi-purpose clips are in an open position thus exposing arm contact faces 202A and 202B. Arm contact faces will be discussed in further detail below for FIGS. 3B-3D. Further illustrated is breakable strip 204A and 204B, which is parted. As noted previously, it may be appreciated that this feature may be utilized to indicate to a surgical team member that the surgical tool holder has been used to secure a surgical tool. If no tool is present in the surgical tool holder and the breakable strip is parted, then this may be an indication that a surgical tool is missing. By identifying the use of the holder, lost tools may be avoided in some examples.

Figure 3A:
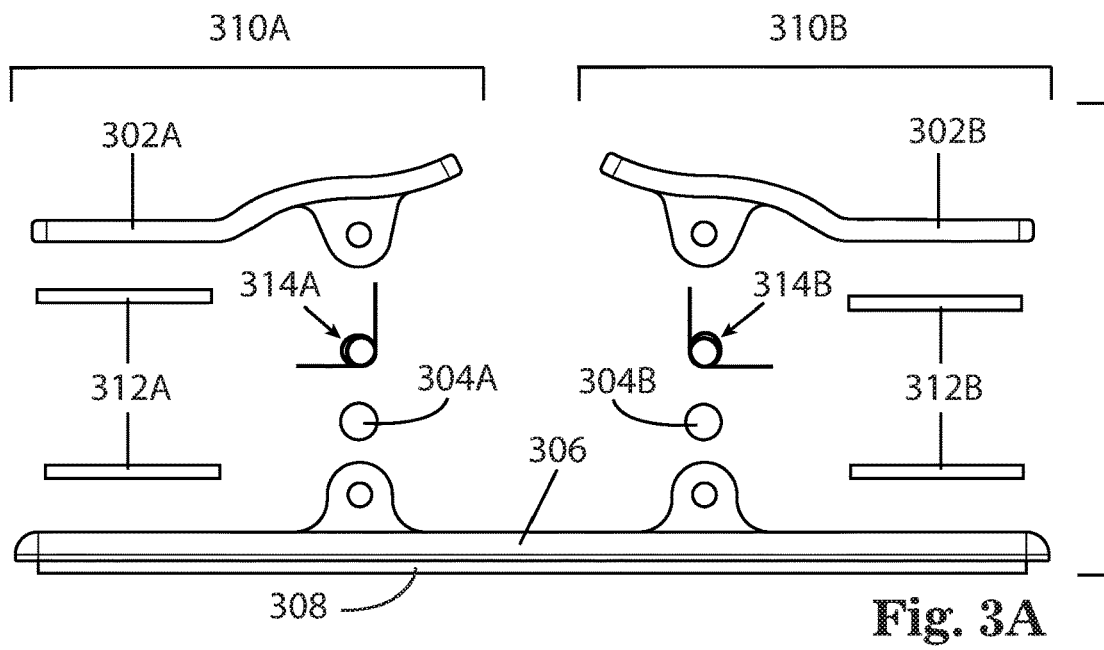
FIGS. 3A-3D are illustrative representations of surgical tool holders in accordance with embodiments of the present invention.

FIGS. 3A-3D are illustrative representations of surgical tool holders in accordance with embodiments of the present invention. In particular FIG. 3A is an exploded illustrative representation of a surgical tool holder. As illustrated, the opposing securing elements presented in this illustration are multi-purpose clips. Multi-purpose clips 310A and 310B may be utilized for securing any number of surgical tools. In addition, by simply changing arm contact faces 312A and 312B of a multi-purpose clip embodiment, a customized gripping surface may be achieved. In embodiments, an arm contact face may be manufactured from a variety of materials including: a foam material, a polymeric material, a hydrophilic material, a rubber material, and a composite material without limitation. As illustrated, multi-purpose clips 310A and 310B may include clamping arm 302A and 302B, which may be pivotally coupled with base 306 via pin 304A and 304B. Clamping springs 314A and 314B provide a closing force for the multi-purpose clamps. In addition, as illustrated, an attachment element or layer 308 may be coupled with base 306 along the base's bottom surface. This attachment element may be utilized to couple the surgical tool holder with a surgical surface. As noted above, at times, a surgeon or surgical team may utilize a portion of a surgical surface such as a surgical curtain to lay out or organize surgical tools. In order to maintain order and secure surgical tools, an attachment element may be utilized to couple the surgical tool holder with the surgical surface. Surgical surfaces may include a surgical curtain, a Mayo stand, and an instrument table without limitation. In addition, attachment element embodiments may include: a snap, a clasp, a clamp, a hook and loop strip, an adhesive tape strip, a fabric pinch, a magnetic strip, and a button without limitation.

Figure 3B:
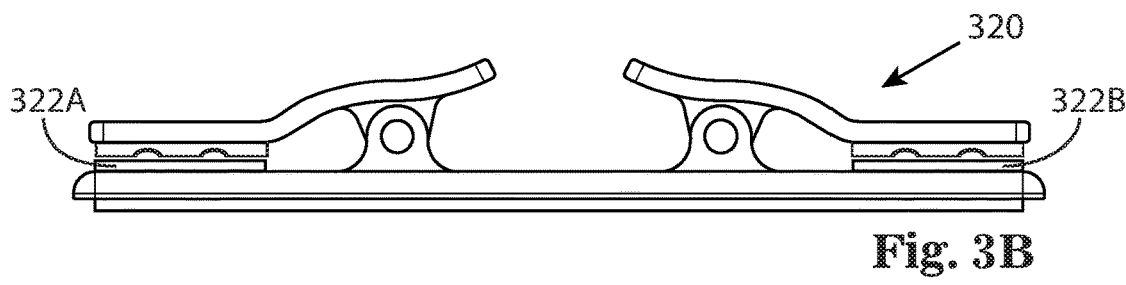
Figure 3C:
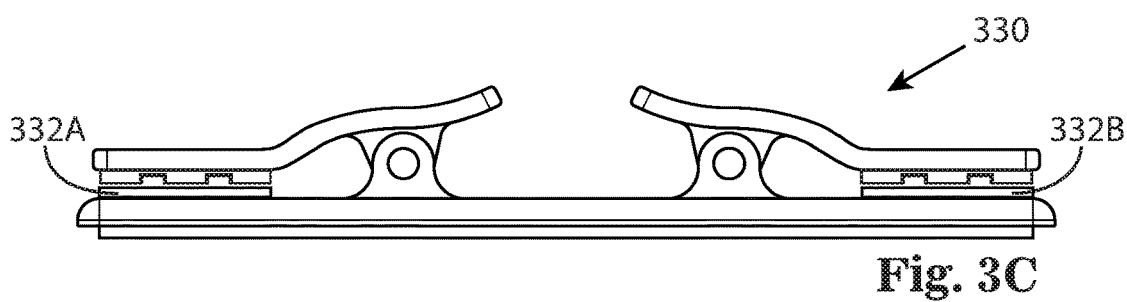
Figure 3D:
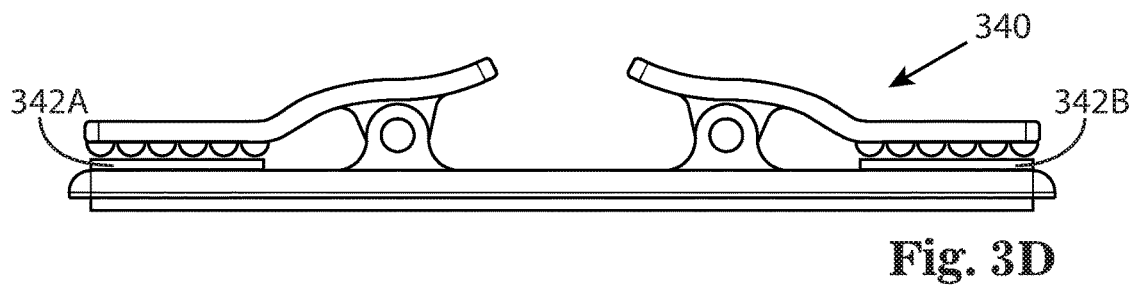

FIG. 3B is an illustrative representation of surgical tool 320 having arm contact faces 322A and 322B each including a curved groove face. In this example, one face is flat and the opposing face includes the curved groove. However, in some embodiments, either face may include one or more curved grooves. FIG. 3C is an illustrative representation of surgical tool 330 having arm contact faces 332A and 332B each including a squared groove face. In this example, one face is flat and the opposing face includes the squared groove. However, in some embodiments, either face may include one or more squared groves. FIG. 3D is an illustrative representation of surgical tool 340 having arm contact faces 342A and 342B each including a ribbed face. In this example, one face is flat and the opposing face includes the ribs, however, in some embodiments, both faces may include ribs. As such, arm contact face embodiments may include: a flat face, a contoured face, a ribbed face, a curved groove face, a squared groove face, and a channeled face without limitation.

Figure 4:
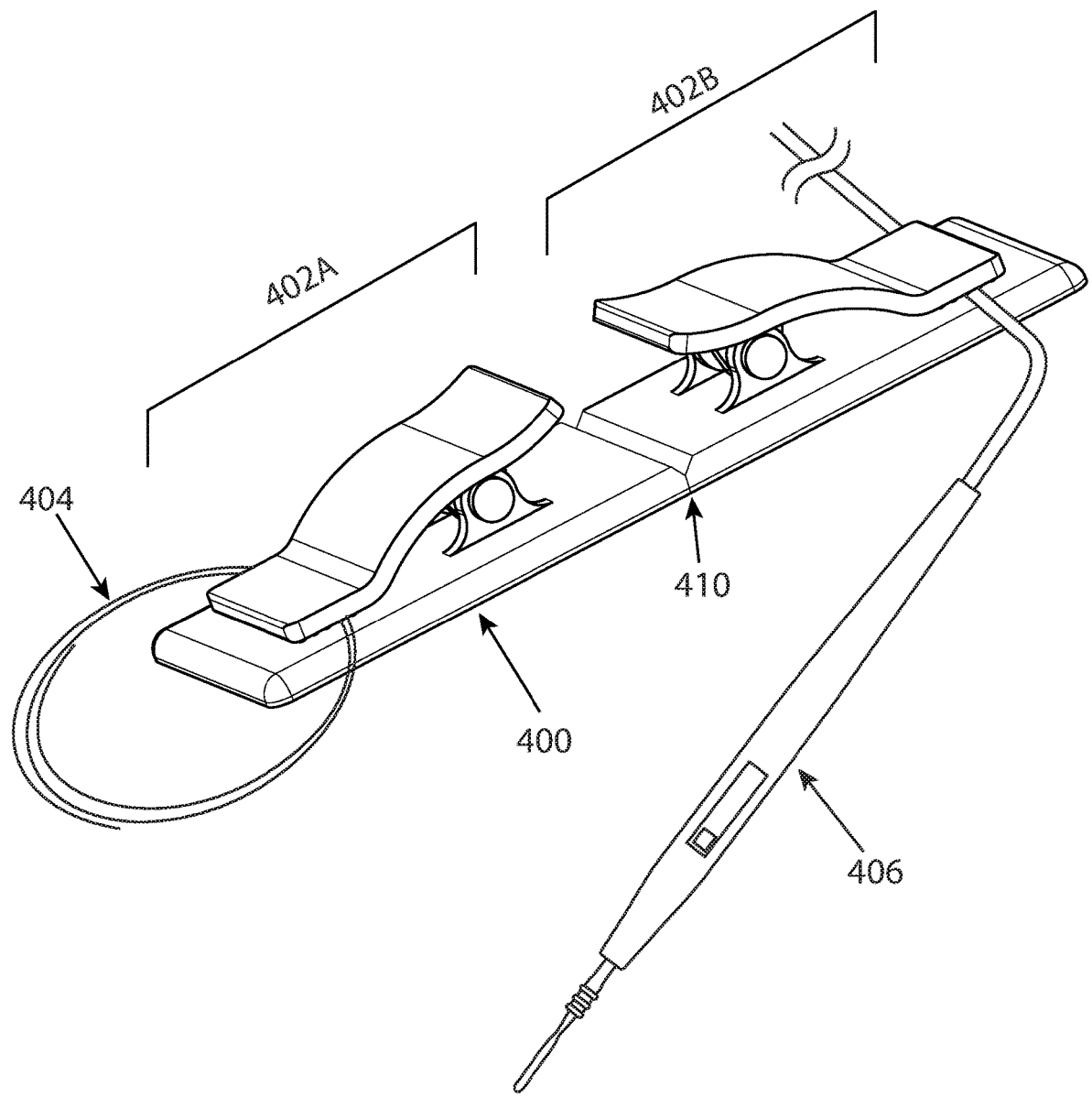
FIG. 4 is an illustrative representation of a surgical tool holder in use in accordance with embodiments of the present invention.

FIG. 4 is an illustrative representation of surgical tool holder 400 in use in accordance with embodiments of the present invention. The opposing securing elements presented in this illustration are multi-purpose clips 402A and 402B. As noted above, multi-purpose clips may be utilized for securing any number of surgical tools. As such, in use, multi-purpose clip 402A may secure suture material 404 while multi-purpose clip 402B may secure surgical tool 406. Any number of surgical instruments, tools, or supplies may be secured using embodiments disclosed herein without limitation. In addition, break line 410 is disposed across the base and may include a grooved or pre-cut feature allowing easy separation of the securing elements. A user may separate the opposing securing elements along break line 410 at any time desired. For example, it may be desirable, in some instances, to break apart surgical tool holders so that a particular instrument may be placed closer to where a surgeon may need it. In other examples, a surgical tool holder may be placed on an area having a smaller footprint. As such, use of a break line allows for different configurations in accordance with a surgeon's wishes.

Figure 5A:
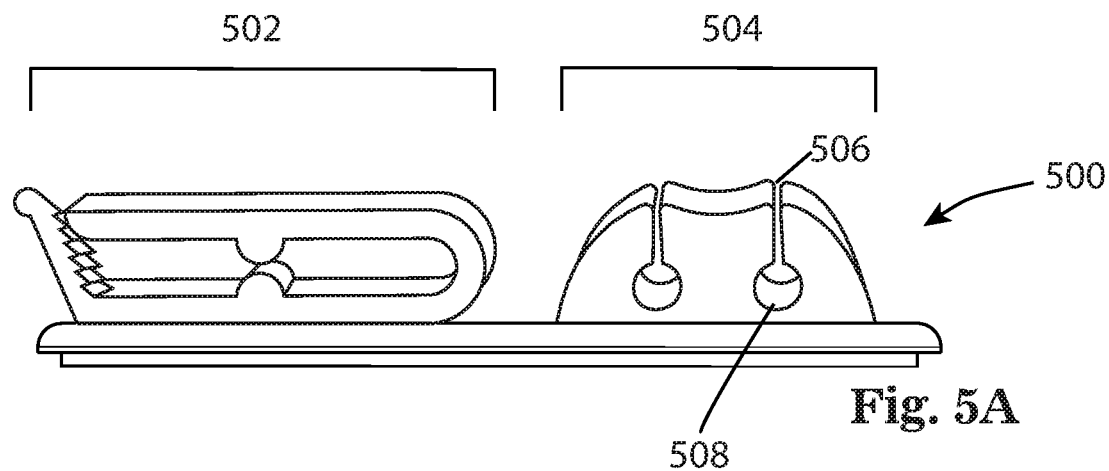
FIGS. 5A-5C are illustrative representations of surgical tool holders in accordance with embodiments of the present invention.
Figure 5B:
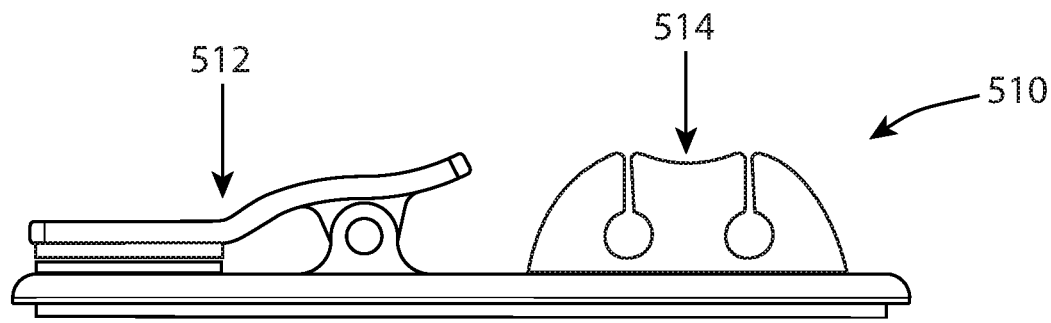
Figure 5C:
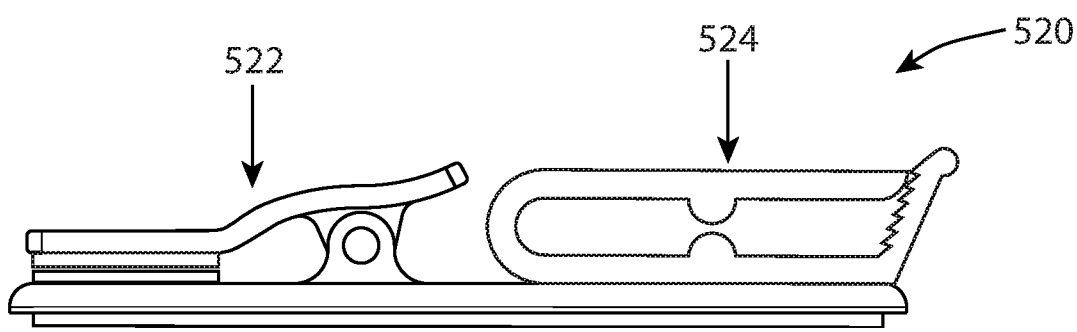

FIGS. 5A-5C are illustrative representations of surgical tool holders in accordance with embodiments of the present invention. For example, FIG. 5A illustrates surgical tool holder 500 having tubing clamp 502 and wire holder 504. Further illustrated, wire holder 504 may include wire channel 506 extending across and downward from a top surface of wire holder 504. In addition, wire holder 504 may include wire cavity 508 extending across wire holder 504 and formed continuously with wire channel 506. In another embodiment, FIG. 5B illustrates surgical tool holder 510 having multi-purpose clip 512 and wire holder 514. In still another embodiment, FIG. 5C illustrates surgical tool holder 520 having multi-purpose clip 522 and tubing clamp 524. These illustrative representations are provided for clarity in understanding various configurations that may be achieved utilizing embodiments disclosed herein and should not be construed as limiting.

Figure 6:
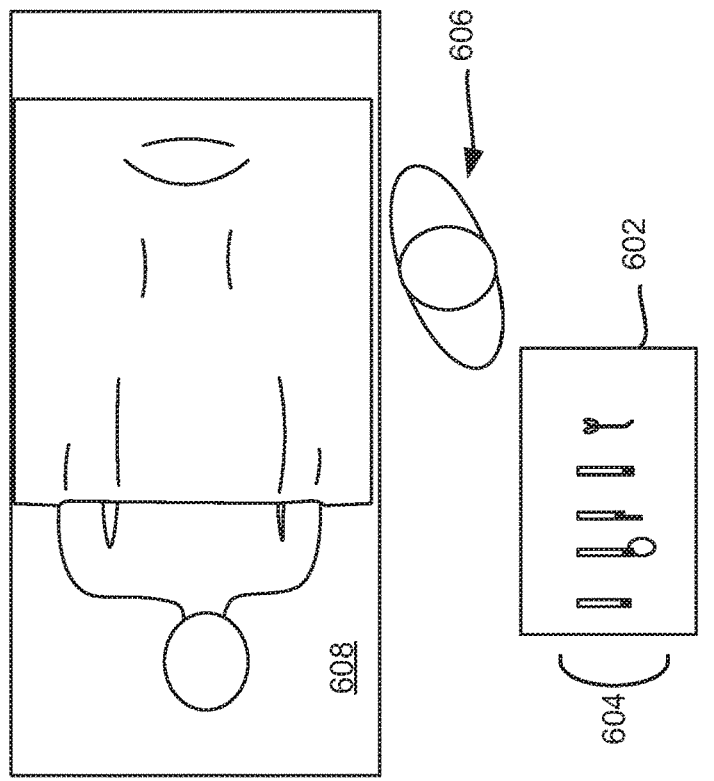
FIG. 6 is an illustrative representation of a prior art surgical tool management system.

FIG. 6 is an illustrative representation of a prior art surgical tool management system 600. Conventionally, surgical tray 602 may be located within easy reach of surgeon 606 performing surgery on patient 608. A variety of surgical instruments 604 may be placed on surgical tray 602 for use in a particular operation. While this method is universally utilized, the reality is that often times tools are placed on the patient or the operating table so that the surgeon's movement may be optimized. That is, rather than continually twisting back and forth, a surgeon may simply place a regularly utilized instrument within easy reaching distance. Because these surfaces may become crowded or may be unstable, instruments may fall to the floor outside the sterile field requiring replacement. This may cause undesirable delays and cost expenditures.

Figure 7:
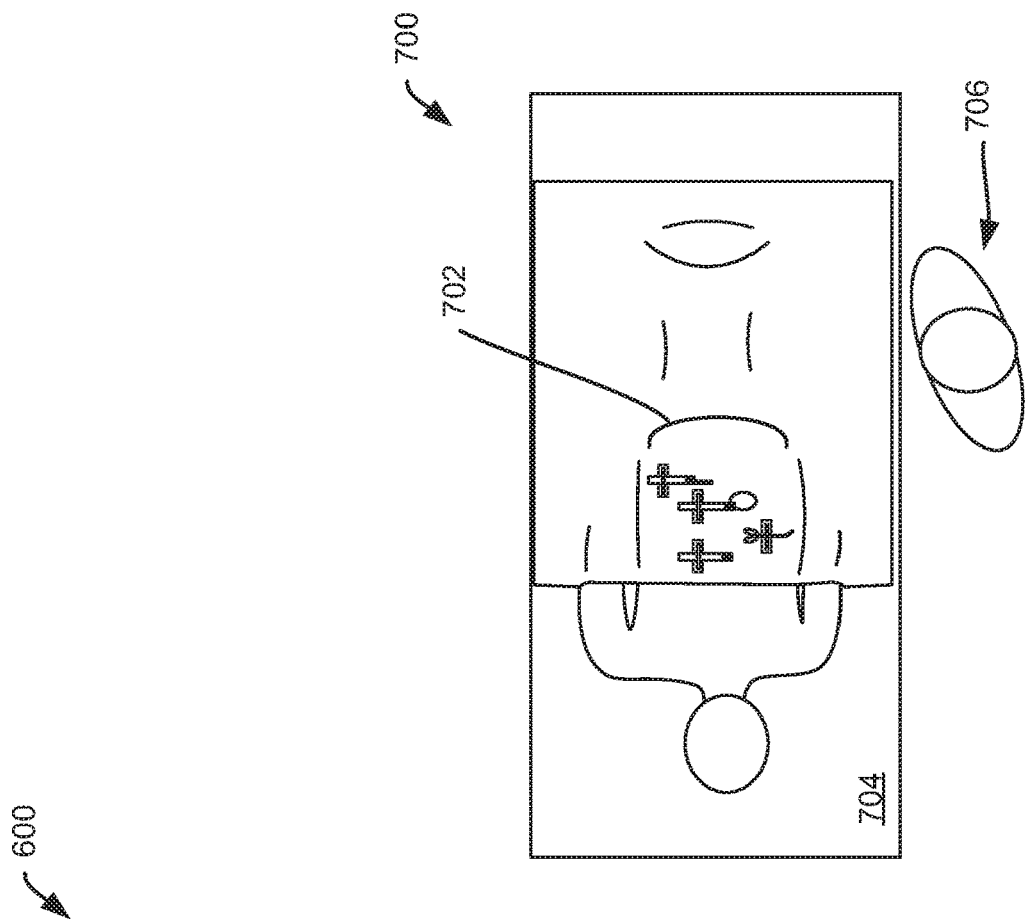
FIG. 7 is an illustrative representation of a surgical tool management system in accordance with embodiments of the present invention.

FIG. 7 is an illustrative representation of surgical tool management system 700 in accordance with embodiments of the present invention. Utilizing embodiments provided herein, a number of instruments 702 may be placed on a surgical curtain within easy reach of surgeon 706 performing surgery on patient 704. Methods for utilizing embodiments may include: providing a surgical surface such as a surgical curtain; providing a number of surgical tool holders for removably securing surgical tools; securing the surgical tool holders with the surgical surface; securing the surgical tools with the surgical tool holders; and during a procedure, removing any of the surgical tools from the surgical tool holder for immediate use. Furthermore, as noted above, in some examples, surgical tools holders may be separated and used individually by separating the holders along a break line.

The terms "certain embodiments", "an embodiment", "embodiment", "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

While this invention has been described in terms of several embodiments, there are alterations, permutations, and equivalents, which fall within the scope of this invention. It should also be noted that there are many alternative ways of implementing the methods and apparatuses of the present invention. Furthermore, unless explicitly stated, any method embodiments described herein are not constrained to a particular order or sequence. Further, the Abstract is provided herein for convenience and should not be employed to construe or limit the overall invention, which is expressed in the claims. It is therefore intended that the following appended claims be interpreted as including all such alterations, permutations, and equivalents as fall within the true spirit and scope of the present invention.

What is claimed is:

1. A surgical tool management system comprising:
   a plurality of surgical tool holders for removably securing a plurality of surgical tools, wherein each of the plurality of surgical tool holders comprises:
   a base, wherein the base includes a top surface, a bottom surface, a first end, and a second end;
   an attachment element coupled with and along the bottom surface, wherein the attachment element removably couples anywhere along any portion of a surgical surface, and wherein
   the attachment element further comprises an adhesive layer, and
   at least two opposing securing elements disposed along and integral with the top surface of the base, wherein
   the at least two opposing securing elements face opposite directions, wherein
   the at least two opposing securing elements are each positioned at the first end and the second end, wherein
   the base further comprises a break line disposed across the base from a first edge to a second edge and between the at least two opposing securing elements to optionally and permanently separate the at least two opposing securing elements from one another, wherein
   each of the plurality of surgical tool holders is individually attachable anywhere along the surgical surface, and wherein
   the opposing securing elements are selected from the group consisting of: a multi-purpose clip, a wire holder, and a tube clamp wherein the wire holder comprises; a wire channel extending across a top surface of the wire holder and downward; and a wire cavity extending across the wire holder and formed continuously with the wire channel.

2. The system of claim 1, wherein the surgical surface is selected from the group consisting of: a surgical curtain, a Mayo stand, and an instrument table.

3. The system of claim 1, wherein the multi-purpose clip comprises:
a clamping arm having an arm contact face;
a clamping spring; and
a pivot pin, and wherein the base further comprises a base contact face.

4. The system of claim 3, wherein the arm contact face and the base contact face is selected from the group consisting of: a flat face, a contoured face, a ribbed face, a curved groove face, a squared groove face, and a channeled face.

5. The system of claim 1, wherein the attachment element is selected from the group consisting of: a snap, a clasp, a clamp, a hook and loop strip, an adhesive tape strip, a fabric pinch, a magnetic strip, and a button.

6. The system of claim 1, wherein each of the opposing securing elements is manufactured from a phosphorescent material, and wherein the opposing securing elements are color coded by surgical function or surgical type.

7. The system of claim 1, wherein the opposing securing elements further comprise a breakable strip along an opening such that the breakable strip is parted upon using the opposing securing elements to indicate that the opposing securing element has been used to secure one of the plurality of surgical tools.

8. A surgical tool holder that removably secures a surgical tool, the surgical tool holder comprising:
a base wherein the base includes a top surface a bottom surface, a first end, and a second end;
an attachment element coupled with and along the bottom surface, wherein
the attachment element removably couples anywhere along any portion of a surgical surface, and wherein
the attachment element further comprises an adhesive layer, and
at least two opposing securing elements disposed along and integral with the top surface of the base, wherein
the at least two opposing securing elements face opposite directions, wherein
the at least two opposing securing elements are each positioned at the first end and the second end, wherein
the base further comprises a break line disposed across the base from a first edge to a second edge and between the at least two opposing securing elements to optionally and permanently separate the at least two opposing securing elements from one another, wherein
each of the plurality of surgical tool holders is individually attachable anywhere along the surgical surface, and wherein the opposing securing elements are selected from the group consisting of: a multi-purpose clip, a wire holder, and a tube clamp wherein the wire holder comprises; a wire channel extending across a top surface of the wire holder and downward; and a wire cavity extending across the wire holder and formed continuously with the wire channel.

9. The surgical tool holder of claim 8, wherein the multi-purpose clip comprises:
a clamping arm having an arm contact face;
a clamping spring; and
a pivot pin, and wherein the base further comprises a base contact face.

10. The surgical tool holder of claim 9, wherein the arm contact face and the base contact face is selected from the group consisting of: a flat face, a contoured face, a ribbed face, a curved groove face, a squared groove face, and a channeled face.

11. The surgical tool holder of claim 8, wherein the attachment element is selected from the group consisting of: a snap, a clasp, a clamp, a hook and loop strip, an adhesive tape strip, a fabric pinch, and a button.

12. The surgical tool holder of claim 8, wherein each of the opposing securing elements is manufactured from a phosphorescent material, and wherein the opposing securing elements are color coded by surgical function or surgical type.

13. The surgical tool holder of claim 8, wherein the opposing securing elements further comprise a breakable strip along an opening such that the breakable strip is parted upon using the opposing securing elements to indicate that the opposing securing element has been used to secure one of the plurality of surgical tools.

14. A method for using a surgical tool management system comprising:
providing a surgical curtain;
providing a plurality of surgical tool holders for removably securing a plurality of surgical tools, wherein each of the plurality of surgical tool holders comprises:
a base, wherein the base includes a top surface a bottom surface, a first end, and a second end;
an attachment element coupled with and along the bottom surface, wherein the attachment element removably couples anywhere along any portion of a surgical surface, and wherein
the attachment element is selected from the group consisting of: a snap, a clasp, a clamp, a hook and loop strip, an adhesive tape strip, a fabric pinch, a magnetic strip, and a button,
at least two opposing securing elements disposed along and integral with the top surface of the base, wherein
the at least two opposing securing elements face opposite directions, wherein
the at least two opposing securing elements are each positioned at the first end and the second end, wherein
the base further comprises a break line disposed across the base from a first edge to a second edge and between the at least two opposing securing elements to optionally and permanently separate the at least two opposing securing elements from one another, wherein
each of the plurality of surgical tool holders is individually attachable anywhere along the surgical surface, and wherein
the opposing securing elements are selected from the group consisting of: a multi-purpose clip, a wire holder, and a tube clamp wherein the wire holder comprises; a wire channel extending across a top surface of the wire holder and downward; and a wire cavity extending across the wire holder and formed continuously with the wire channel;
securing the plurality of surgical tool holders with the surgical curtain;

securing the plurality of surgical tools with the plurality of surgical tool holders; and during a procedure, removing any of the plurality of surgical tools from any of the plurality of surgical tool holders for immediate use.

\* \* \* \* \*